United States Patent [19]
Higgs et al.

[11] 4,044,603
[45] Aug. 30, 1977

[54] CONSISTOMETER WITH AUTOMATIC SHUT-DOWN

[75] Inventors: Kenneth O. Higgs, Port Neches; Lawrence F. Marsch, Port Arthur, both of Tex.

[73] Assignee: Texaco Inc., New York, N.Y.

[21] Appl. No.: 719,628

[22] Filed: Sept. 1, 1976

[51] Int. Cl.² .......................................... G01N 11/14
[52] U.S. Cl. .......................................................... 73/59
[58] Field of Search ...................................... 73/54, 59

[56] References Cited
U.S. PATENT DOCUMENTS

| 3,668,677 | 6/1972 | Higgs | 73/59 X |
|---|---|---|---|
| 3,812,706 | 5/1974 | Higgs et al. | 73/59 |

Primary Examiner—Richard C. Queisser
Assistant Examiner—Joseph W. Roskos
Attorney, Agent, or Firm—Thomas H. Whaley; Carl G. Ries; Ronald G. Gillespie

[57] ABSTRACT

A consistometer continuously measures the consistency of a stream of material flowing through it which is provided by apparatus manufacturing the material. The consistometer includes a resilient member located in the stream of material and a reference member located outside of the stream of material and both members rotate synchronously. Sensor spatially related to the rotating members provide corresponding signals. A circuit connected to the reference member sensor provides reference member pulses in accordance with the reference member sensor sensing the passage of the reference member and a second circuit connected to the resilient member sensor provides resilient member pulses in accordance with the resilient member sensor sensing passage of the resilient member. A network provides an output corresponding to the consistency of the material in accordance with the reference member pulses and the resilient member pulses. The consistometer also includes circuitry for shutting down the apparatus so as to stop the material manufacturing process when there is a rotational failure of the consistometer or invalid signals provided by the sensors.

4 Claims, 3 Drawing Figures

CONSISTOMETER WITH AUTOMATIC SHUT-DOWN

BACKGROUND OF THE INVENTION

1. Field of the Invention

The present invention relates to measuring apparatus in general and, more particularly, to consistometers.

2. Description of the Prior Art

Consistometers, heretofore, the type disclosed in U.S. Pat. No. 3,812,706, which issued on May 28, 1974 and is assigned to Texaco Inc., assignee of the present invention, provided a graphical record of the consistency of material being measured. Should the consistometer have a rotational failure or signals provided by the sensors be invalid, the material continued to be manufactured. The present invention provides for an automatic shut-down of the apparatus manufacturing the material along with and indicating light when there is a rotational failure of the consistometer or when the sensed signals are invalid.

Similarly, the consistometer of the type disclosed in U.S. Pat. No. 3,668,677, which issued on June 6, 1972 and is assigned to Texaco Inc., assignee of the present invention, only provided an alarm when spurious signals occur instead of valid signals.

SUMMARY OF THE INVENTION

A consistometer, which continuously measures the consistency of a stream of material provided by appratus manufacturing the material includes a rotatable resilient member located in the stream and a reference member located outside of the stream. The two members are rotated synchronously. The consistometer also includes two sensors, each sensor sensing the passage of a corresponding member and provides a signal in accordance with the passage of the member. A circuit connected to the sensors provides an enabling pulse in accordance with the signals from the sensors. A comparator connected to the sensor sensing the passage of the reference member compares the signal from that sensor with a predetermined voltage corresponding to an acceptable signal level when enabled by the enabling pulse from the circuit and provides a comparison signal of one level when the reference member signal is an acceptable signal and of another level when the reference member signal is not an acceptable signal or when the comparator has not been enabled by an enabling pulse. Pulse circuits connected to the comparator and to the resilient member sensor provides a reference member pulse and a resilient member pulse in accordance with the comparison signal and the resilient member signal, respectively. A flip-flop receiving the reference member pulses and the resilient member pulses provides a signal corresponding to the consistency of the material in accordance with the pulses. An output circuit responsive to the signal from the flip-flop for providing an output corresponding to the consistency of the material. A control network connected to the flip-flop shuts down the apparatus when the flip-flop fails to provide a signal corresponding to the consistency of the material.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustrative purposes only and are not to be construed as defining the limits of the invention.

DESCRIPTION OF THE INVENTION

Figure 1:
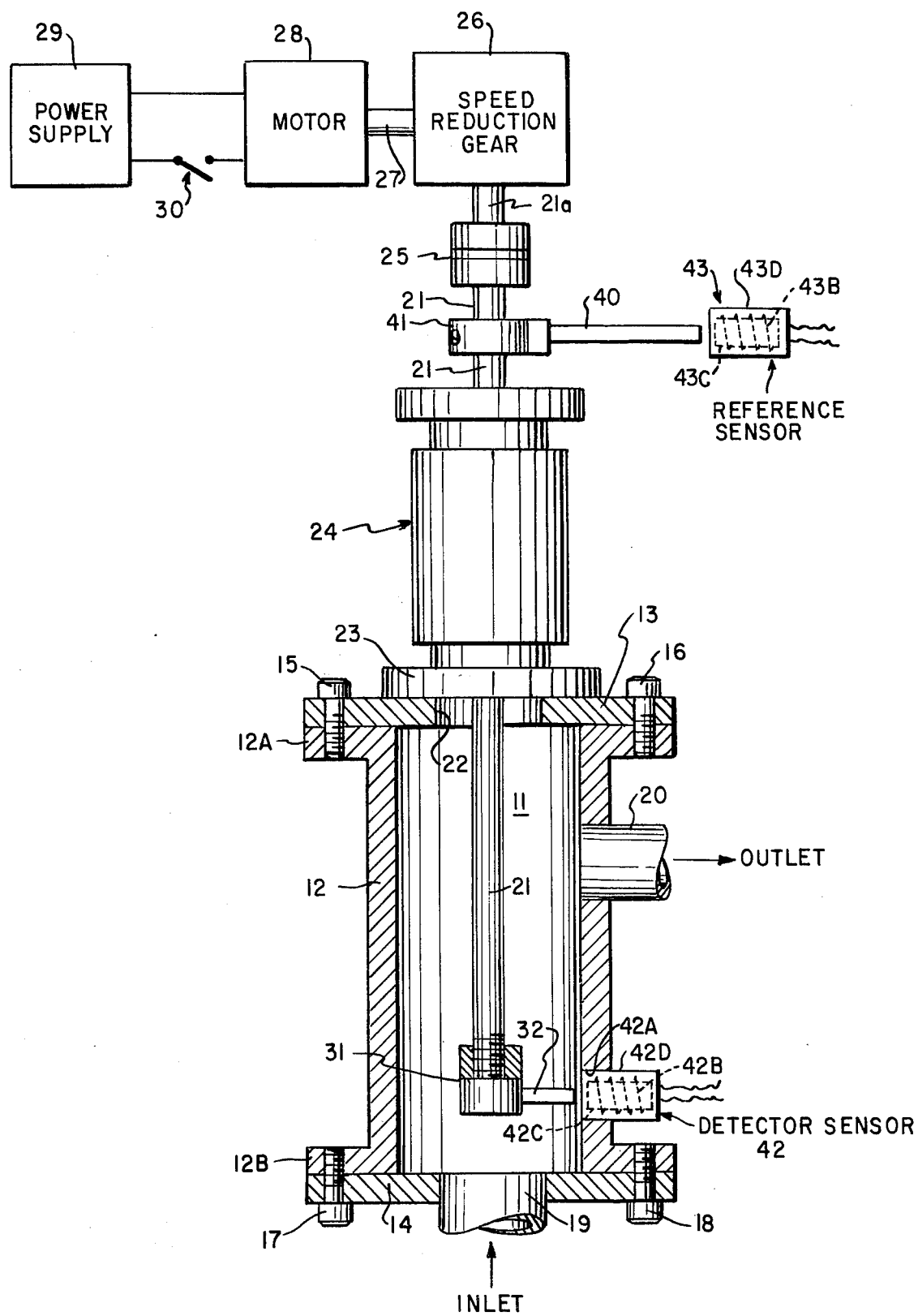
FIG. 1 is a combined simplified block diagram and a mechanical view of a portion of a consistometer constructed in accordance with the present invention.

Referring now to FIG. 1, there is shown consistometer apparatus embodying features of the present invention, wherein a chamber 11 is defined by tubular side walls 12 of appropriate steel or other material suitable to maintain the grease or other material whose consistency is to be measured and having upper and lower end plates 13, 14 bolted to respective upper and lower flanges 12A, 12B on chamber member 12 by means of bolts 15, 16, 17, 18. At the lower end of chamber 11, in lower end plate 14, there is provided an opening for receiving an inlet conduit 19 through which material, such as grease, the consistency of which is to be measured, may be introduced under appropriate pressure in a continuous stream. An outlet conduit 20 is provided at an upper portion of sidewall 12 of chamber 11 for outputting a stream of the material passing through chamber 11 for consistency measurement. Directly above inlet conduit 19, axially aligned therewith, there is provided a shaft 21 extending into chamber 11 through an opening 22 in upper plate 13 from a stuffing box arrangement 23 containing appropriate means for sealing fluid within the chamber under appropriate pressure from bearings (not shown) in a bearing assembly 24 through which shaft 21 extends upwardly to a mechanical coupling 25 from whence it is driven by means of a speed reduction gear 26 which, in turn, is coupled by means of a drive shaft 27 to an electric motor 28. Electric motor 28 provides means for driving shaft 21 at a constant speed and is, in turn, electrically coupled to a suitable power supply 29 through appropriate conductors including a switch 30.

The lower end of shaft 21 within chamber 11 has affixed thereto a mounting assembly 31, shown threaded to the lower end of shaft 21, for attaching a resilient reference blade member 32 to shaft 21. Blade 32 is mounted to shaft 21 so that the two surfaces about which it is flexible are parallel to the direction of the flow of the material in the stream passing upwardly from inlet 19 through chamber 11 and thence out through outlet 20. Shaft 21 including assembly 31 and resilient member 32 mounted thereon are rotated at a constant rate as the material being measured is passed through chamber 11 in the direction of the arrow shown below inlet 19 in the drawing. Blade 32 may be formed of steel capable of deflection in the material being measured, such as grease, and the end of the blade will be deflected as it rotates in the material by an amount dependent upon the reaction forces exerted thereon by the material as an indication of the consistency of such material.

Means are provided for substantially continously measuring the amount of deflection or flexure of resilient member 32 as a measure of the consistency of the material passing through chamber 11.

A reference member 40 is mounted on shaft 21 by means of a mounting assembly 41 which may be in the form of a collar having an appropriate set screw therein for facilitating adjustment of the position of member 40 on shaft 21 relative to the position of resilient member 32 on shaft 21, as will be discussed in further detail hereinafter. It will be seen from the above that resilient member 32 and relatively rigid member 40, both being mounted to shaft 21, will rotate in synchronism as the shaft is rotated by motor 28.

In a preferred embodiment resilient member 32 and relatively rigid reference member 40 are mounted to shaft 21 so that they lie in substantially the same plane as the central axis of shaft 21 when resilient member 32 is in its normal position, i.e., not subjected to forces tending to deflect same. The reference and the "resilient" members may also lie in a different plane, but such is not necessary.

Figure 2:
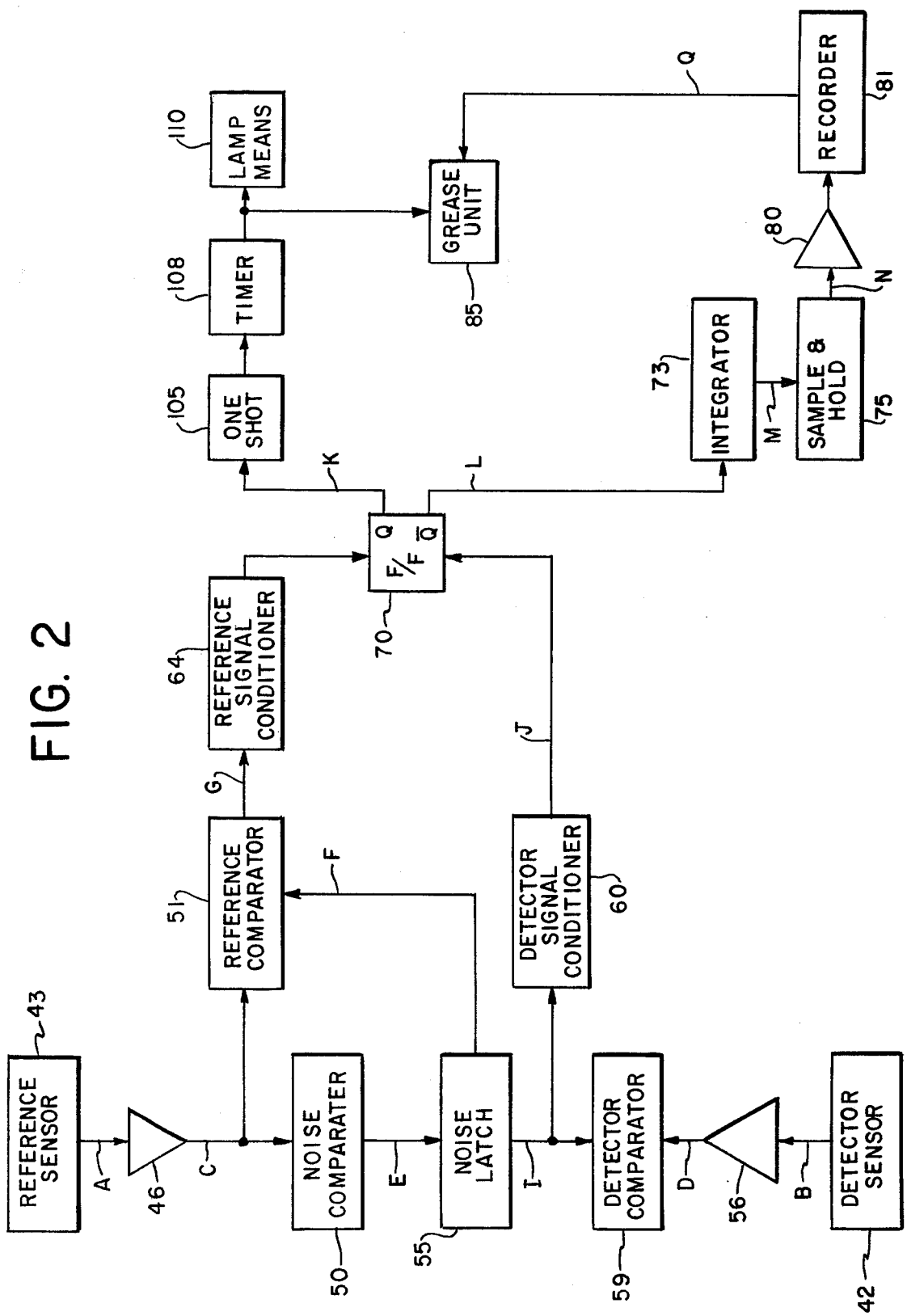
FIG 2 is a simplified block diagram of the remaining portion of the consistometer constructed in accordance with the present invention.

When shaft 21 is rotated in a stream of material, such as grease, reaction forces of such material upon resilient member 32 will cause it to be deflected to an extent dependent upon the consistency of the material. Means are provided for measuring this deflection of member 32 comprising a first detector or sensor, referred to as detector sensor 42, opposite the resilient member 32, and a second detector or sensor, referred to as reference sensor 43, opposite rigid member 40. Sensors 42, 43, preferably comprise magnetic sensors responsive to the passage or respective blades 32 and 40. By measuring the time difference between the passage of blades 32, 40 relative to their respective magnetic sensors 42 and 43, it is possible to determine the amount of deflection of blade 32 in the material passing through the chamber 11 as a means for measuring the consistency thereof. Such time differences can be measured by the use of appropriate electrical circuitry as described in further detail hereinafter, with particular reference to FIG. 2.

It is to be noted that, in the preferred embodiment, sensors 42, 43 advantageously comprise respective magnetic sensors mounted within relatively rugged shells or housings formed of stainless steel or the like to withstand the conditions and materials encountered within chamber 11 as the stream of material being measured passes through. Sensor 42 is shown mounted within an opening 42A in wall 12 of chamber 11, whereby the magnetic sensor is able to detect flexible detector blade 32 magnetically, without itself being placed within the material passing through chamber 11. Reference sensor 43 is mounted through the use of appropriate means (not shown) for maintaining it opposite rigid reference blade member 40 so that the reference sensor 43 may sense or detect reference member 40 magnetically as it moves past same. Advantageously, the magnetic sensor of sensor 43 may also be mounted within a casing of stainless steel or the like similar to that employed for enclosing sensor 42.

It will be appreciated that rigid reference member 40 is shown mounted to shaft 21 at a location outside of chamber 11. This is the preferred embodiment, since it permits adjustment of the reference blade. However, it is possible to construct apparatus of the type herein disclosed wherein rigid reference member 40 is mounted to a portion of shaft 21 within chamber 11. In such event, rigid member 40 should be affixed to the shaft at a position downstream from the flexible blade (above flexible 32, as shown in FIG. 1) a sufficient distance to avoid producing any adverse effect on the consistency of the material flowing through chamber 11 prior to its passing flexible member 32. In a further embodiment, as described in detail hereinafter, the reference member may comprise a nonmagnetic disc with a magnetic inset, in which event the likelihood of turbulence within chamber 11 is substantially eliminated.

In the event that reference member 40 should be positioned within chamber 11, it may be desirable to provice a longer chamber 11 than otherwise so that reference member 40 can be spaced beyond the position where it might otherwise influence the consistency of the material whose consistency being measured by flexible member 32. In the latter event, reference sensor 43 should be positioned within an opening in side wall 12 of chamber 11 in a manner similar to the positioning of sensor 42 and may advantageously be positioned between the location of outlet 20 and the upper end of chamber 11 as shown in FIG. 1.

It is to be appreciated that member 32 is here described as flexible in comparison to rigid reference member 40. It is to be understood that the rigidity of member 40 is a relative term, depending upon its environment. Accordingly, when mounted outside of chamber 11 so that member 40 is in the surrounding air, it will not need to be so rigid or still as when positioned within chamber 11 for rotation in the material being measured as discussed above.

It is also to be appreciated that although flexible member 32 are reference member 40 are shown positioned in the same plane, it is possible to position the two members in different planes displaced around the axis of shaft 21 or otherwise mount same for rotation in synchronism, so long as the two sensors are positioned opposite the respective members such that when there is no material in chamber 11 or when the resilient detector member is stationary in the material in chamber 11, the two members are in phase at their zero points, namely, flexible member 32 and rigid member 40 are both opposite the center of respective sensors 42, 43 at the same time such that when rotated in flowing material under operating conditions flexible member 32 will be deflected from the corresponding rotational point of reference member 40 by an amount that is measurable by means of the respective detectors 42, 43 for determination of the amount of flexure of blade 32 due to the consistency of the material passing through chamber 11.

Figure 3:
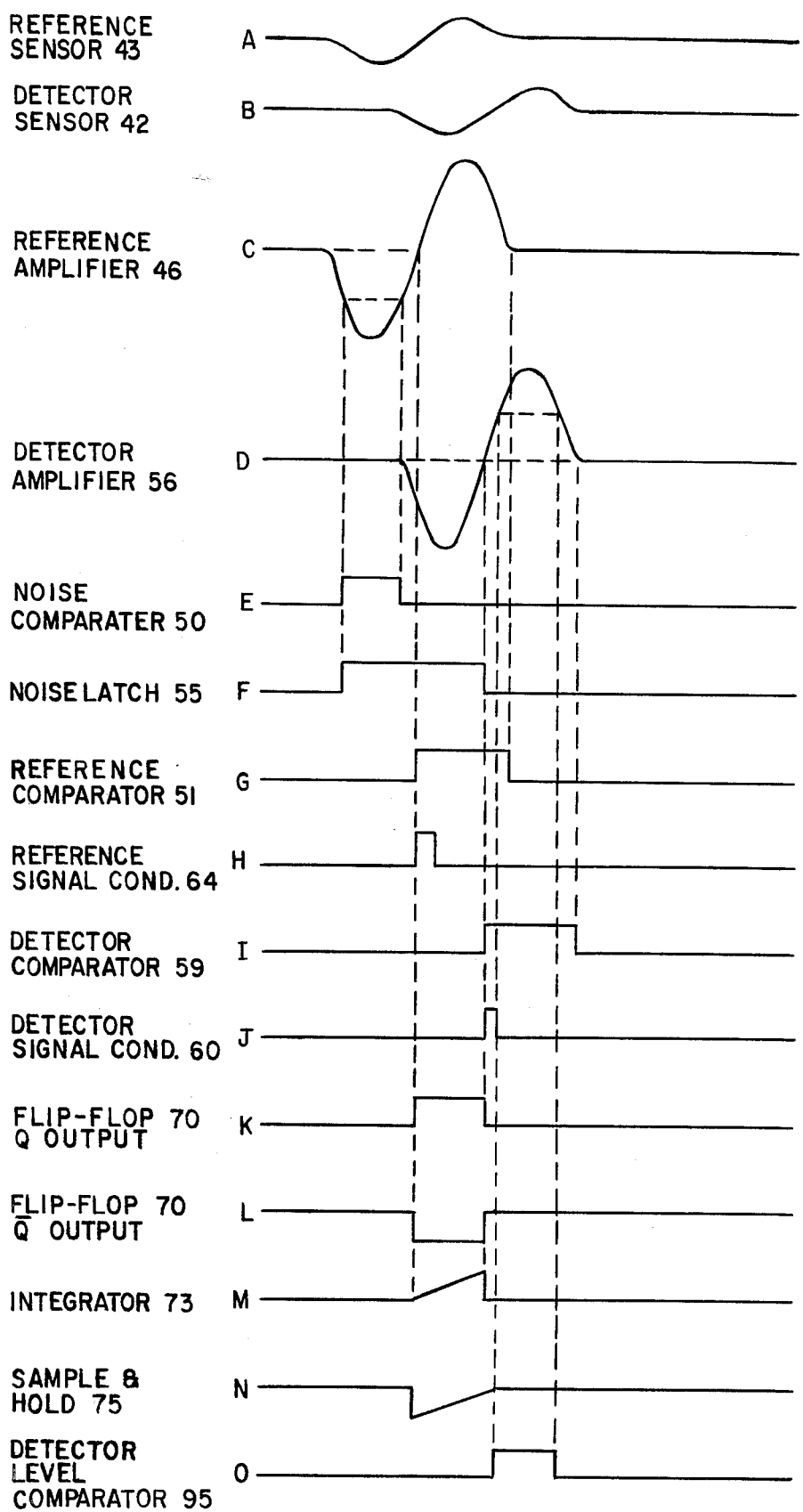
FIGS. 3A through 3O are graphical representations of signals occurring within the consistometer during operation thereof.

Reference sensor 43 provides a signal A, as shown in FIG. 3A, to a reference amplifier 46 which provides an output C, shown in FIG. 3C, to a noise comparator 50 and to a reference comparator 51. As shown in FIG. 3C, the output C of amplifier 46 is similar to a one cycle sine wave for each passage of member 40 past reference sensor 43, going from a zero reference to a negative peak swinging back to positive peak and then to zero. Noise comparator 50 is a conventional type comparator receiving a negative signal (not shown) of a predetermined value corresponding to a noise level. An output E provided by noise comparator 50, shown in FIG. 3E, is at a zero level until signal C exceeds the noise level indicating that signal C is a valid signal at which time signal E rises to a high logic level and remains there until signal C again drops below noise level. Noise comparator 50 provides signal E as a pulse having a duration corresponding to the length of time that the negative peak of signal C exceeds the noise level. Signal E is applied to a noise latch 55.

Similarly the output of detector sensor 42, shown in FIG. 3B, is amplified by an amplifier 56 to provide a signal D, shown in FIG. 3D, corresponding to the passage of member 32 past detector sensor 42. Signal D is applied to a detector comparator 59 and to a detector level comparator 95. Detector comparator 59 receives a positive signal (not shown) corresponding to a predetermined acceptable signal from detector amplifier 56 and provides a signal I, shown in FIG. 3I, to noise latch 55. The amplitude of the positive signal is close to zero, so as signal D goes from a negative to positive, signal I from comparator 59 goes to a high level.

The operation of noise latch 55 is such that when noise comparator 50 determines that signal C is not noise, signal E causes noise latch 55 to provide a signal F, shown in FIG. 3F, at a high logic level which is applied to reference comparator 51 enabling comparator 51 to make a comparison of signal C. When signal A is noise, signal C causes comparator 50 to provide signal E at a low level and therefore noise latch 55 is not able to provide signal F at a high level so that comparator 51 cannot compare the noise being provided by amplifier 46. As signal C precedes signal D, signal F initially goes to a high level in response to an output from comparator 50. Detector comparator 59 detecting that there is a signal D provides signal I at a high level to noise latch 55 to reset it causing signal F to go to a low level and thus prevent the comparison of any noise coming out of amplifier 46.

Reference comparator 51 provides signal G at a high level in response to the reference signal C crossing the zero reference line going from a negative peak to a positive peak where it remains until signal C returns to its zero level causing signal G to go to a low level thereby forming a pulse. Duration of that pulse has no significant meaning. However, the leading edge of the G pulse is conditioned by reference signal conditioner 64 to provide a pulse H, shown in FIG. 3H, to a flip-flop 70. Flip-flop 70 provides its Q and $\bar{Q}$ outputs as signals K and L, respectively, shown in FIGS. 3K and 3L, respectively. Signals K, L are at high and low levels, respectively, when flip-flop 70 is in a set state, and are at reversed levels when flip-flop 70 is in a clear state. Flip-flop 70 is triggered by pulse H to a set state.

In response to signal I going to a high level, detector signal conditioner 60 provides a pulse J, shown in FIG. 3J, to flip-flop 70 which resets flip-flop 70 to a clear state. The time duration when signals K, L were at a high and a low level, respectively, corresponds to the consistency of the material. An integrator 73 integrates signal L to provide an output M, shown in FIG. 3M, to a sample and hold circuit 75. Sample and hold circuit 75 provides a signal N, corresponding to the material's consistency, in accordance with signal M to an amplifier 80. Amplifier 80 amplifies signal N and provides it to a recorder 81. Recorder 81 provides a signal Q to a grease unit 85 for controlling the grease unit.

The operation of the consistometer as hereinbefore described in similar to that of consistometers disclosed and described in the aforementioned U.S. Pat. No. 3,812,706 and 3,668,677. The present embodiment calls for a consistometer that controls the grease unit and indicates that there is a rotational failure or an inadequate sensed signal. A one-shot multivibrator 105 recieves signal K from flip-flop 70. As signal K changes from a low level to a high level periodically during normal operation, it triggers one-shot 105 causing one-shot 105 to provide a reset pulse to a timer 108. With timer 108 being reset periodically, it provides a low output to grease unit 85 and lamp means 110. Grease unit 85 continues to manufacture grease and lamp means 110 is not lit while the output from timer 108 is at a low level.

Should the consistomer experience a rotational failure, or either the reference member signal A or the resilient member signal B, or both, be absent, signal K from flip-flop 70 will not change levels. Thus one-shot 105 does not provide a reset pulse. When timer 108 reaches a predetermined count, it provides a high level output which lights lamp means 110 and shuts down grease unit 85.

The apparatus of the present invention as hereinbefore described is a consistometer having the capability of shutting down a corresponding grease unit when the consistometer experiences a rotational failure or the absence of a sensed signal.

What is claimed is:

1. A consistometer for continuously measuring the consistency of a stream of material from apparatus manufacturing the material comprising a rotable resilient member located in said stream so that the opposite surfaces about which said member is flexible are substantially parallel to the direction of flow in said stream, means for rotating said member at a constant rate about an axis which is parallel to the direction of flow in said stream, a reference member, means for rotating the reference member in synchronism with the resilient member, resilient member sensing means spatially related to the resilient member for providing a resilient member signal in accordance with the movement of the resilient member, reference member sensing means spatially related to the reference member for providing a reference member signal in accordance with the movement of the reference member, noise means connected to both sensing means for providing an enabling pulse in accordance with the reference member signal and the resilient member signal, first comparison means connected to the reference member sensing means and to the noise means for comparing the reference member signal with a predetermined voltage, corresponding to an acceptable reference member signal level, when enabled by an enabling pulse, and providing a first comparison signal at one level when the reference member signal is an acceptable signal and at another level when it is not acceptable and for not making the comparison when the noise means does not provide an enabling pulse when not making the comparison; reference member pulse means connected to the first comparison means for providing a reference member pulse in response to the first comparison signal going from the other level to the one level; resilient member pulse means connected to the resilient member sensing means for providing a resilient member pulse in accordance with the resilient member signal; a flip-flop connected to both pulse means provides a signal corresponding to the consistency of the material, in accordance with the resilient member pulses and the reference member pulses; output means connected to the flip-flop for providing an output corresponding to the consistency of the material in accordance with the signal from the flip-flop; and control means connected to the flip-flop and to the apparatus for controlling the apparatus in accordance with the signal from the flip-flop so that the apparatus continues to manufacture the material when the flip-flop provides a signal which alternately changes level and to prevent the apparatus from manufacturing the material when the signal from the flip-flop does not change levels.

2. A consistometer as described in claim 1 in which the control means includes a one-shot multivibrator connected to the flip-flop and responsive to changes in the level of the signal from the flip-flop to provide reset pulses and not to provide the reset pulses when the signal from the flip-flop does not change levels; and timer means connected to the one-shot multivibrator and to the apparatus for providing a control signal at one level, which permits the apparatus to continue to manufacture the material, until a predetermined time interval, after the timer means has been reset, has elapsed and at another level, which causes the apparatus to stop manufacturing the material after the predetermined time interval has elapsed and until the timer means is reset, said timer means being reset by the reset pulses from the one-shot multivibrator and where the time between reset pulses during normal operation of the consistometer is less than the predetermined time interval.

3. A consistometer as described in claim 2 further comprising indicating means connected to the timer means and responsive to the control signal for indicating whether the consistometer is permitting the apparatus to continue to manufacture the material or the consistometer has stopped the manufacturing of the material.

4. A consistometer as described in claim 3 in which the indicating means is lamp means which provides no light when the control signal is at the one level and which provides light when the control signal is at the other level.

* * * * *